United States Patent
Nowosielski

(10) Patent No.: US 6,302,864 B1
(45) Date of Patent: Oct. 16, 2001

(54) APPARATUS AND METHOD FOR DELIVERING FLUID FLOW TO A SURGICAL SITE

(75) Inventor: Albert Nowosielski, Roselle, IL (US)

(73) Assignee: Northgate Technologies, Inc, Elgin, IL (US)

( * ) Notice: Subject to any disclaimer, the term of this patent is extended or adjusted under 35 U.S.C. 154(b) by 0 days.

(21) Appl. No.: 09/397,904

(22) Filed: Sep. 17, 1999

Related U.S. Application Data

(63) Continuation of application No. 08/762,025, filed on Dec. 11, 1996, now Pat. No. 6,030,359.

(51) Int. Cl.$^7$ .................................................. A61M 31/00
(52) U.S. Cl. ............................. 604/65; 604/67; 604/500; 604/131
(58) Field of Search ...................... 604/500, 35, 65–67, 604/131, 4.01, 29, 31–33, 145, 48; 128/DIG. 24; 222/95

(56) References Cited

U.S. PATENT DOCUMENTS

| | | |
|---|---|---|
| Re. 32,303 | 12/1986 | Lasker et al. . |
| 3,578,774 | 5/1971 | McDonald, Jr. et al. . |
| 3,927,671 | 12/1975 | Chittenden et al. . |
| 4,180,074 | 12/1979 | Murry et al. . |
| 4,240,408 | 12/1980 | Schael . |
| 4,252,115 | 2/1981 | Schael . |
| 4,275,726 | 6/1981 | Schael . |
| 4,303,068 | 12/1981 | Zelman . |
| 4,306,976 | 12/1981 | Bazzato . |
| 4,379,453 | 4/1983 | Baron . |
| 4,381,003 | 4/1983 | Buoncristiani . |
| 4,412,917 | 11/1983 | Ahjoalo . |
| 4,585,436 | 4/1986 | Davis et al. . |
| 4,600,401 | 7/1986 | Kamen . |
| 4,657,160 | 4/1987 | Woods et al. . |
| 4,838,856 | 6/1989 | Mulreany et al. . |
| 4,994,026 | 2/1991 | Fecondini . |
| 4,998,914 | 3/1991 | Wiest et al. . |
| 5,061,241 | 10/1991 | Stephens, Jr. et al. . |
| 5,152,746 | 10/1992 | Atkinson et al. . |
| 5,163,900 | 11/1992 | Wortrich . |
| 5,176,629 | 1/1993 | Kullas et al. . |
| 5,178,606 | 1/1993 | Orgnier et al. . |
| 5,338,293 | 8/1994 | Jeppsson et al. . |
| 5,382,229 | 1/1995 | Gabenkort et al. . |
| 5,464,391 | 11/1995 | DeVale . |
| 5,497,912 | 3/1996 | Hoback et al. . |
| 5,563,584 | 10/1996 | Rader et al. . |
| 5,605,545 | 2/1997 | Nowosielski et al. . |
| 5,720,728 | 2/1998 | Ford . |
| 5,722,947 | 3/1998 | Jeppson et al. . |
| 5,800,383 | * 9/1998 | Chandler et al. ...................... 604/35 |
| 5,830,180 | * 11/1998 | Chandler et al. ...................... 604/65 |
| 6,004,443 | * 12/1999 | Rhodes et al. ...................... 204/454 |
| 6,030,359 | 2/2000 | Nowosielski . |

FOREIGN PATENT DOCUMENTS 2 378 494  10/1980  (FR) .

OTHER PUBLICATIONS

U.S. application No. 08/762,671, Nowosielski et al., filed Dec. 11, 1996.

\* cited by examiner

*Primary Examiner*—Richard K. Seidel
*Assistant Examiner*—Kevin C. Sirmons
(74) *Attorney, Agent, or Firm*—Brinks Hofer Gilson & Lione

(57) ABSTRACT

An irrigation apparatus and a method of use for delivering fluid flow to a surgical site. The irrigation apparatus includes a refillable fluid reservoir with an inlet for receiving fluid via first tubing from a fluid source, and an outlet for second tubing leading to a surgical site. A sensor monitors the fluid contained within the reservoir. The sensor sends a signal to a controller, which operates a pump. The pump transports fluid from the fluid source to the refillable reservoir via the first tubing.

19 Claims, 3 Drawing Sheets

APPARATUS AND METHOD FOR DELIVERING FLUID FLOW TO A SURGICAL SITE

This is a continuation of U.S. Ser. No. 08/762,025 filed Dec. 11, 1996, U.S. Pat. No. 6,030,359, which application is hereby incorporated by reference.

BACKGROUND OF THE INVENTION

The present invention relates to an apparatus and method for delivering fluid flow to a surgical site. In particular, the present invention relates to an irrigation apparatus and method that can provide continuous and adjustable pressurized fluid flow from a fluid source to a surgical site.

Many types of surgical procedures require irrigation at surgical sites. For example, such surgical procedures include urological procedures and arthroscopic procedures. In these procedures, the surgeon may desire a continuous source of fluid not only to flush the surgical area of loose tissue or other debris which may cause post-operative complications, but also to maintain uncluttered visualization of and access to the surgical site.

One conventional method of providing irrigation during a surgical procedure is to hang one or more bags of saline (or other suitable irrigating fluid, such as "ringers solution", sterile water, normal saline, sorbitol, manitol, 2% glycine, and so on) from an adjustable IV pole. The outlets of the bags are connected to one end of a length of plastic tubing. The other end of the tubing connects to the surgical instrument or otherwise is provided to the site. The bags may be suspended from heights of up to 6 to 8 feet or more above the patient in order to achieve the desired pressure and/or fluid flow rate. This conventional method is easy-to-use, well understood, and economical. However, this conventional method has several drawbacks.

One drawback of this procedure is that the maximum pressure that can be delivered is limited by the height of the ceiling. An additional drawback may occur as the contents of the bags run low. At that time, a medical attendant may be required to hoist replacement bags to an inconvenient level or even climb a ladder to reach the position where the empty fluid bags are suspended. Yet another drawback is that during the time it takes for the bags to be replaced, the surgeon may be forced to suspend the operation due to interruption of the irrigation fluid flow.

An additional problem sometimes associated with the conventional irrigation technique is waste. It is likely that the tubing sets and unused irrigation fluid will be discarded at the termination of the procedure due to sterility concerns. Consequently, additional fluid reining in the fluid bags will have to be discarded, which may contribute to overall medical costs.

Accordingly, one object of the present invention is to provide an irrigation apparatus that allows uninterrupted fluid flow to a surgical site. Another object is to provide an irrigation apparatus that allows uninterrupted fluid flow to a surgical site with a relatively constant pressure. Still another object is to provide an irrigation apparatus that is economical and easy to operate. Yet still another object is to provide an irrigation system that minimizes the inconvenience or hazard associated with lifting heavy, awkward bags of fluid to heights necessary to provide the required pressure. An even further object is to provide an irrigation apparatus that minimizes waste of unused irrigation fluid and/or tubing.

SUMMARY OF THE INVENTION

To address the above concerns, the present invention provides a method and an apparatus for delivering fluid to a surgical site. The apparatus includes a refillable fluid reservoir. The delivery of the fluid from the fluid reservoir to the surgical site is pressurized by suitable means, such as by suspending the reservoir at a desired height above the patient on an adjustable IV pole or imparting a compressive force on the reservoir. A pump transports fluid from a primary fluid source, such as saline bags, to the refillable fluid reservoir. A sensor monitors the fluid contained within the fluid reservoir. The sensor sends an output to a controller to determine when the reservoir should be refilled. The controller is adapted to operate the pump in order to maintain a desired amount of fluid within the reservoir. Tubing connects the fluid source to the refillable reservoir and also connects the reservoir to the surgical site.

DETAILED DESCRIPTION OF THE PRESENTLY PREFERRED EMBODIMENTS

First Embodiment

Figure 1:
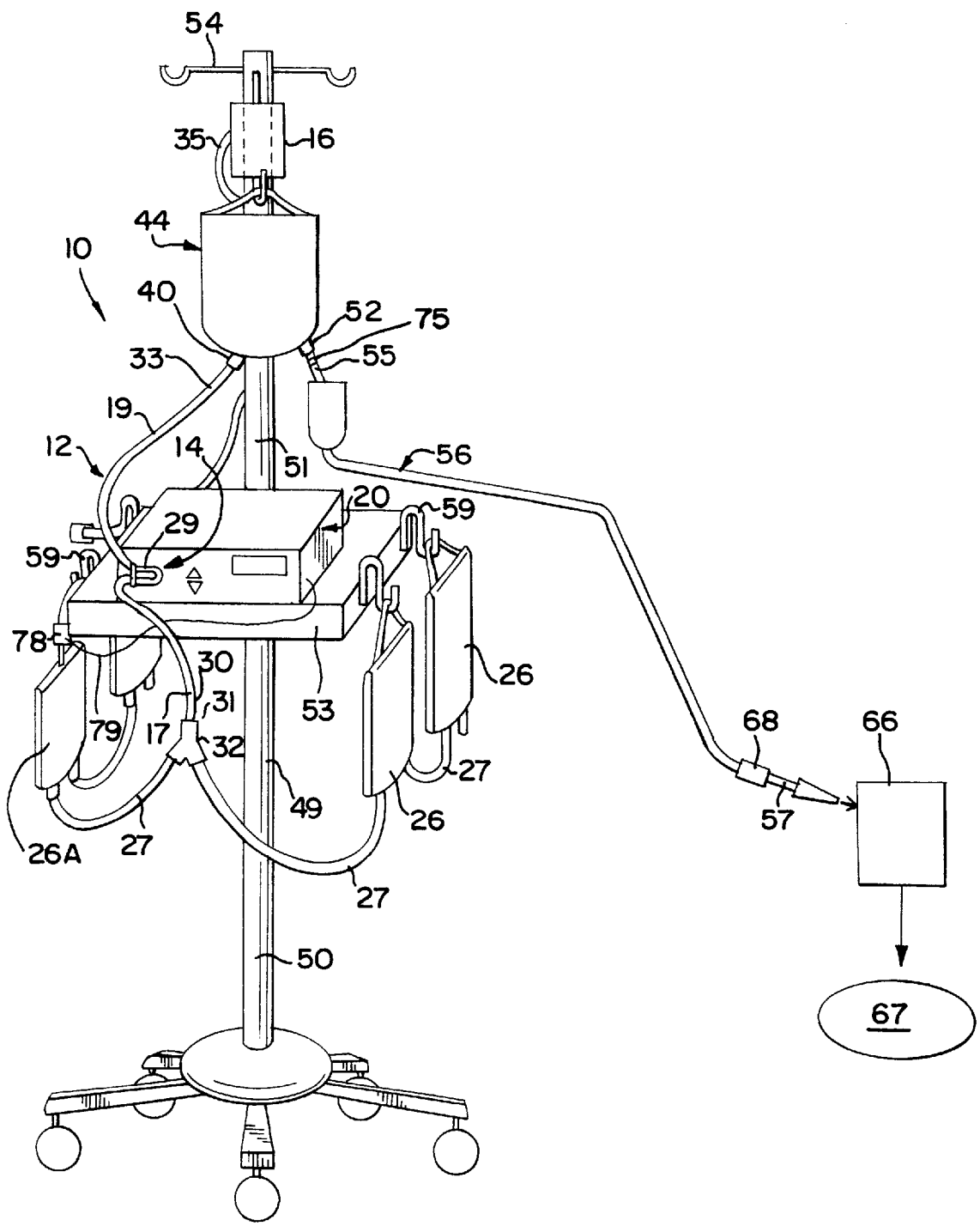
FIG. 1 is a diagram of an irrigation system according to a first embodiment of the present invention.
Figure 2:
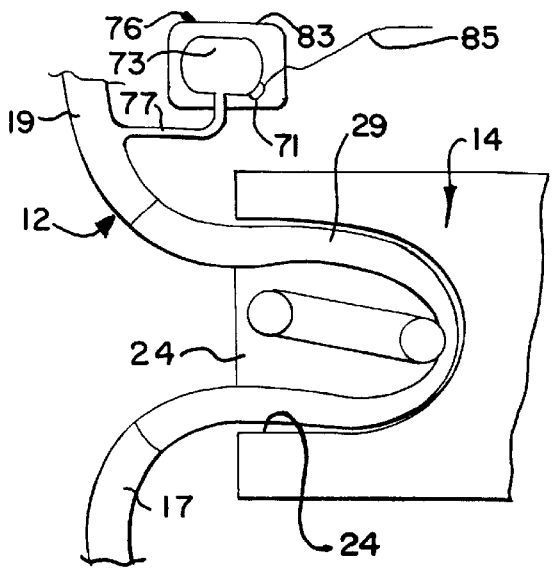
FIG. 2 is an enlarged side view including the intermediate section of the first tubing portion of the embodiment of FIG 1.
Figure 3:
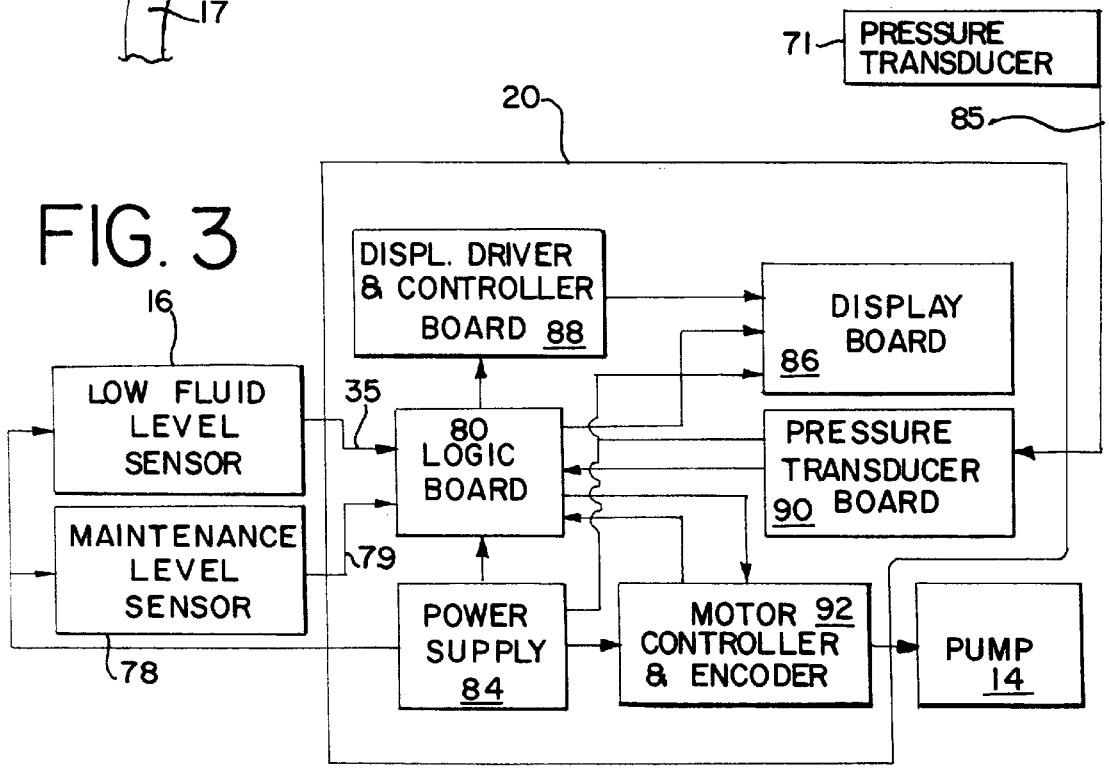
FIG. 3 is a block diagram of the controller in the embodiment of FIG. 1.

A first embodiment of an irrigation apparatus 10 for delivering continuous pressurized flow to a surgical instrument is shown in FIGS. 1–3. The apparatus 10 can deliver a continuous supply of fluid at a constant pressure during a surgical procedure and avoids the awkward lifting of heavy bags filled with fluid.

A plurality of fluid bags 26 containing a suitable irrigation fluid are provided. Suitable fluids include normal saline, "ringers solution", sterile water, sorbitol, manitol, 2% glycine, and so on. The plurality of bags 26 are interconnected via conventional tubing 27 so that one bag or all of the fluid can flow together to a single outlet 31, which may be formed as part of a "Y" connector 32. The plurality of fluid bags 26 can be suspended from hooks 59 attached to a shelf 53, which is mounted to a portion 49 of a standard IV pole 50. The shelf 53 may be mounted at a convenient height, such as 3 or 4 feet from the floor, in order to facilitate easy access to the plurality of fluid bags 26.

A first tubing portion 12 includes a first or proximal section 17, a second or distal section 19, and an intermediate section 29 located between and connecting the first and second sections 17 and 19. A proximal end 30 of the proximal tubing section 17 connects to and extends from the single outlet 31. A distal end 33 of the second tubing section 19 connects to an inlet 40 of a fluid reservoir 44. The intermediate section 29, located between and connecting the first and second sections 17 and 19, interacts with a pump 14. In this embodiment, the pump 14 is a positive displacement pump and the intermediate section 29 is received in the track 24 of positive displacement pump, as shown in FIG. 2. The positive displacement pump 14 may be a peristaltic pump. The pump 14 is located on the shelf 53 that is mounted to the portion 49 of the standard IV pole 50.

The fluid reservoir 44 is suspended from a hook 54 locked near the top of a vertically adjustable portion 51 of the standard IV pole 50. In the present embodiment, a conventional bag of saline may be used for the fluid reservoir 44. A first end 55 of a second tubing portion 56 extends from an outlet 52 of the fluid reservoir 44 to a surgical site 67. A second end 57 of the second tubing portion 56 may connect to a surgical instrument 66 or other apparatus, such as a scope, to provide irrigation to the surgical site 67. A manually-operable clamp valve 68 is located along the length of the second tubing portion 56. The clamp valve 68 may be used as needed to close off fluid flow to the surgical site 67 or the surgical instrument 66. The clamp valve 68 can also be used to shut off reverse flow backwards to the fluid reservoir 44. Further, in a present embodiment, a check valve 75 is located in the second tubing portion 56 close to first end 55 thereof. The check valve 75 is used to shut off reverse flow backwards to the fluid reservoir 44.

Referring to FIG. 2, in a preferred embodiment, the first tubing portion 12 includes a pressure sensor assembly 76. The pressure sensor assembly 76 is coupled to the second tubing section 19 by means of a short section of tubing 77. The short section of tubing 77 connects to the second tubing section 19 immediately downstream of the intermediate section 29 in the peristaltic pump 14. The pressure sensor assembly 76 includes a relatively rigid housing 83 that encases a bulb 73. The bulb 73 communicates via the short section of tubing 77 with the second tubing section 19 and therefore conveys the pressure in the second tubing section 19 to the pressure sensor assembly 76. Located in the housing 83 between an inside wall of the housing and the bulb 73 is a pressure transducer 71. In this location, the pressure transducer 71 is responsive to the pressure in the housing 83 and therefore to the pressure in the second tubing section 19. The pressure transducer 71 provides an output 85 (via a lead by any other suitable means of data transmission) to a controller 20.

Referring again to FIG. 1, a first sensor 16 is mounted near the top of the vertically adjustable portion 51 of the standard IV pole 50. The first sensor 16 is responsive to a property or a state of the fluid located within the fluid reservoir 44. The output signal is indicative of the property or state of the fluid located within the fluid reservoir 44. In this embodiment, the first sensor 16 operates to measure the weight (or volume of the fluid reservoir 44. The first sensor 16 sends an output signal 35 over a wire lead to the controller 20. Alternatively, the output 35 from the first sensor 16 may be transmitted to the controller 20 by any suitable mode of data transmission, e.g. optical, cabling, wireless transmission, and so on.

In a preferred embodiment, a second sensor 78 is coupled between one of the plurality of bags, e.g. bag 26A, and the one of the hangers 59 from which the bag 26A is suspended from the shelf 53. In a present embodiment, the second sensor 78 is also a weight sensor. The second sensor 78 may be identical to the first sensor 16. This one bag 26A is suspended so that it is at a lesser height than all the rest of the plurality of bags 26. This one bag 26A is suspended so that the second sensor 78 is responsive to the weight of fluid in the bag 26A. The second sensor 78 provides an output 79 to the controller 20 via suitable means, such as a wire lead, etc.

The controller 20 may be located inside the housing that also includes the pump 14. The controller 20 provides an output that operates the positive displacement pump 14. Alternatively, the pump 14 may be operated at the discretion of the user.

FIG. 3 shows block diagram of the controller 20. The controller 20 includes a logic board 80, a power supply 84, a display board 86, a display driver and controller board 88, a pressure transducer board 90 and a motor controller and encoder 92. The logic board 80 is a conventional type of board and has inputs 81 and 82 that receive the signals 35 and 79 from the first and second sensors 16 and 78 respectively. The logic board 80 provides outputs to the display board 86 and the motor controller and encoder 92. The power supply 84 receives power from a suitable source, such as line current, and provides power to the logic board 80, the sensors 16 and 78, the display board 86, the pressure transducer board 90, and the motor controller and encoder 92. The display driver and controller board 88 receives an output from the logic board 80 and provides an output to the display board 86. The motor controller and encoder 92 provides an output to the pump 14.

The controller 20 includes a pressure transducer board 90 that receives the output 85 from the pressure transducer 71. The pressure transducer board 90 provides an output to the logic board 80 indicative of the pressure sensed by the pressure transducer 71 in the housing 83.

The following describes one exemplary embodiment the first tubing portion 12 and the second tubing portion 56 are constructed of PVC, silicone, or other biocompatible tubing material. The intermediate section 29 of the first tubing portion 12, that interacts with the pump 14, is molded, while the remainder of the first tubing portion 12 is extruded. The first tubing portion 12 is approximately 3–12 feet long. The first tubing portion 12 has an outer diameter of approximately ⅜ inches and an inner diameter of approximately ¼ inches. The intermediate portion 29 of the first tubing portion 12 has an outer diameter of approximately ⅜ inches, an inner diameter of approximately ¼ inches, and is approximately 8 inches in length. The second tubing portion 56 has on outer diameter of approximately ⅜ inches, an inner diameter of approximately ¼ inches, and is approximately 8 feet in length. The fluid reservoir 44 has a volume of approximately 3 liters, and is composed of PVC. The positive displacement pump 14 may operate to pump approximately 2 liters of fluid per minute. In one embodiment, the pump is peristaltic pump manufactured by Barnant Company. The pressure transducer 71 may be a conventional pressure transducer, such as a model manufactured by Foxboro.

Operation of the Irrigation Apparatus

Referring to FIGS. 1–3, to operate the irrigation system for a surgical procedure, the user estimates the approximate volume of fluid that will be used during the surgical procedure and suspends the plurality of fluid bags 26 corresponding to the approximate volume needed from the hooks 59 attached to the shelf 53 mounted to the portion 49 of the standard IV pole 50.

The first end 30 of the first tubing portion 12 may be connected to a single bag or to the single outlet 31 from the plurality of fluid bags 26. The intermediate portion 29 of the first tubing portion 12 is guided into the track 24 of the peristaltic pump 14. The second end 33 of the first tubing portion 12 is attached to the inlet 40 of the fluid reservoir 44. The first end 55 of the second tubing portion 56 is connected to the outlet 52 of the fluid reservoir 44. The second end 57 of the second tubing portion 56 may be connected to the surgical instrument 66 or another apparatus that delivers fluid to the surgical site 67.

The apparatus 10 is self primed so that fluid fills the first tubing portion 12 as well as the second tubing portion 56. The user determines the approximate pressure and/or flow rate desired at the surgical site, and raises the reservoir bag 44 using adjustable portion 51 of the IV pole 50 accordingly.

The user may enter parameters into the controller 20 that may cause the controller 20 to operate the peristaltic pump 14 or alternatively may use default parameters. The sensor 16—continuously, at regular intervals, or whenever the amount of fluid in the reservoir 44 runs low, as indicated by the weight of the reservoir 44—responds to the volume of fluid in the fluid reservoir 44 and outputs a signal to the controller 20. The controller 20 compares the information received from the sensor 16 with the parameters. If the information received from the sensor 16 is outside the parameters, the controller 20 sends an operational signal to the pump 14. For example, if the input parameters indicate that the fluid reservoir 44 should contain between 2.0 and 2.5 liters of fluid, and the sensor 16 signals the controller 20 that less than 2.0 liters, or an equivalent weight thereof, of fluid are present in the fluid reservoir 44, the controller 20 activates the pump 14, which transports fluid from the fluid bags 26 to the fluid reservoir 44. The pump 14 will operate until the volume in the fluid reservoir 44 reaches 2.5 liters. As the volume of fluid in the fluid reservoir 44 reaches the desired 2.5 liters, the signal sent by the sensor 16 will be analyzed by the controller 20 which will compare the 2.5 liters present in the fluid reservoir 44 with the 2.5 liters as the operating parameters, and will signal the pump 14 to shut off.

If the surgeon desires to interrupt the fluid flow from the fluid reservoir 44 to the surgical site 67, the clamp valve 68 on the second tubing portion 56 may be used. Alternatively, if the second end 57 of the second tubing portion 56 is attached to a surgical instrument 66, the surgeon may engage a shut-off valve located thereon.

Additional replacement fluid bags 26 may be added to the irrigation apparatus 10 as needed during the course of the surgery. For example, if the fluid bags run low and require replacement during the surgical procedure, the first tubing section 12 is clamped off. Since the reservoir bag 44 remains connected to the surgical instrument, all of the fluid source bags 26 may be replaced at the same time without interrupting the surgical procedure since fluid continues to be provided to the surgical instrument 66 from the reservoir 44 while the bags 26 are replaced. Consequently, an uninterrupted, continuous source of fluid is available to the surgeon during the surgical procedure.

In a preferred embodiment, the physician can automatically be warned when the fluid in the plurality of bags 26 runs low. As mentioned above, the second sensor 78 is responsive to the weight in the bag 26A which is suspended lower than the other bags. Thus, during operation, the fluid in the other bags will be withdrawn first. When the fluid in the lowest bag 26A runs low, the low weight is sensed by the second sensor 78. The controller 20 monitors the outputs 79 of the second sensor 78 and provides an alarm, either visual or auditory, when the weight of the low bag 26A is low indicating that the fluid in the plurality of bags has run low.

In a preferred embodiment, the system can also automatically prevent the accidental application of too much pressure. As mentioned above, the controller 20 receives the output 85 from the pressure transducer 71 indicative of the pressure sensed by the pressure transducer 71 in the housing 83 which is essentially the pressure immediately downstream of the pump 14. The controller 20 can be programmed to use this output 85 to monitor for overpressure conditions. When the transducer 71 provides an output indicative of an overpressure condition, e.g. 6 psi, the controller 20 provides an output to the pump 14 to slow down or stop operation of the pump 14 until the overpressure condition subsides.

When the surgical procedure is completed, the surgeon may clamp the irrigation apparatus 10 at a convenient location, such as with the clamp valve 68, or activate the shut-off valve on the surgical instrument 66 to stop fluid flow to the surgical site 67. In the event the surgeon plans to conduct another surgical procedure soon, the irrigation apparatus 10 may be reused without the need for being completely re-fitted with the first tubing portion 12, and the plurality of fluid bags 26. The reservoir 44 serves as a trap that prevents the fluid from flowing backwards upstream of the fluid reservoir 44. In addition, the check valve 75 positioned close to the inlet 55 of the second tubing portion 56 serves to prevent contamination of the reservoir bag 44. The outlet 52 of the fluid reservoir 44 may be clamped and a new, sterile second tubing portion 56a attached to the outlet 52 of the fluid reservoir 44 without compromising the sterility of the entire irrigation system, thereby providing the cost savings associated with reusing the first fluid portion 12, fluid reservoir 44, and the plurality of fluid bags 26.

Because fluid is pumped from a primary source, or fluid bags 26, to a secondary source, or fluid reservoir 44, and from the secondary source to the surgical site 67, the pulsating activity of the pump 14 is not passed on through the second tubing portion 56 to the surgical site 67 Consequently, the surgeon is assured of smooth and even fluid delivery to the surgical site 67

Second Embodiment

Figure 4:
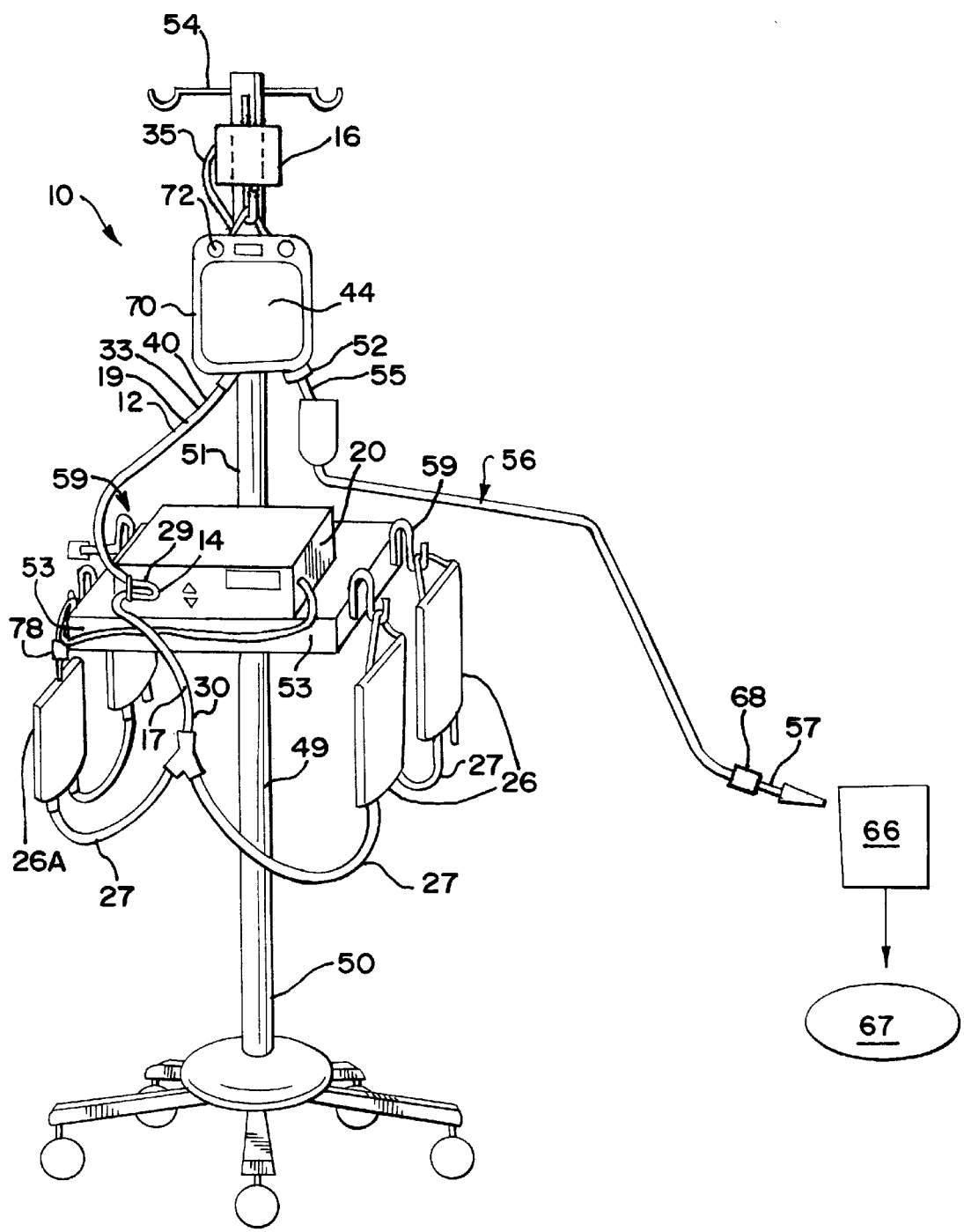
FIG. 4 is a diagram of an irrigation system according to a second embodiment of the present invention.

Referring to FIG. 4, a second embodiment of an irrigation apparatus is shown. This embodiment includes essentially the same elements as those described above. In addition, the irrigation apparatus in this embodiment includes a pressure device 70. The pressure device 70 imparts pressure to the fluid in the second tubing portion 56. In this embodiment, the pressure device 70 imparts pressure to the fluid in the second tubing portion 56 by applying pressure to the fluid in the reservoir 44. When the pressure device 70 is used, the user of the irrigation apparatus 10 does not have to raise the reservoir bag 44 in order to obtain the desired pressure at the surgical site 67.

The pressure device 70 may be of a type commercially available, such as an adjust pressure applicator which is capable of adjustably regulating pressure from a range of 0–500 mm Hg. For example, the pressure device may take the form of an inflatable cuff or cup that encompasses a conventional fluid bag. In one embodiment, the pressure device 70 may be similar to a blood pressure cuff that is wrapped around the fluid reservoir bag. In another embodiment, the pressure device 70 may include a molded relatively rigid housing into which a bag of fluid, i.e. the reservoir bag, may be positioned. An inflatable panel inside the housing is adjustably inflated to apply a desired pressure onto the reservoir bag. Additionally, the pressure device 70 may be operable via connection with fluid or gas sources in proximity to the surgical area.

In operation, the user would attach the pressure device 70 to the fluid reservoir 44 prior to the priming stage and activation of the pump 14. Using this embodiment avoids the requirement that the fluid reservoir 44 be suspended from the adjustable portion 51 of the IV pole 50 because pressure from the fluid reservoir 44 to the surgical site 67 is provided and controlled by the pressure device 70. Accordingly, the reservoir bag 44 may be located on the shelf 53, if desired. The desired fluid pressure can be adjusted through manipulation of settings 72 on the pressure device.

Third Embodiment

Figure 5:
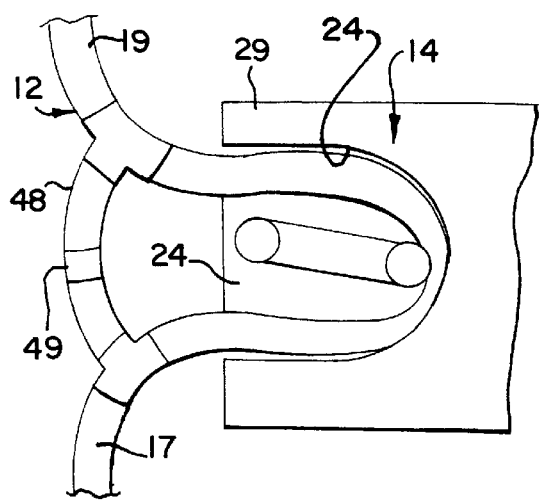
FIG. 5 is an enlarged side view including the intermediate section of a first tubing portion of another embodiment.

Referring to FIG. 5, a portion of a third embodiment of an irrigation apparatus is shown. The portion of the embodiment shown in FIG. 5 corresponds to the portion depicted in FIG. 2, i.e., the intermediate section of the first tubing portion located in the track of the peristaltic pump. The remaining portions of the embodiment of the irrigation apparatus of FIG. 5 may be similar or identical to the embodiments shown in FIGS. 1 or 4. The embodiment of FIG. 5 differs from the embodiments of FIGS. 1 and 4 in that the embodiment of FIG. 5 does not include a pressure sensor assembly 76. Instead, the embodiment of FIG. 5 includes a bypass section 48. The bypass section 48 connects the first tubing section 17 and the second tubing section 19 and is in parallel with the intermediate section 29. The bypass section 48 includes a valve 49 which in a preferred embodiment is a pressure relief valve. The threshold value of the pressure relief valve 49 is selected so that it opens when the pressure on the downstream side of the valve (corresponding to the second tubing section 19) exceeds the pressure on the upstream side of the valve (corresponding to the first tubing section 17) by a chosen amount. The bypass section 48 is located outside of the pump 14 and provides a pressure relief flow path from the downstream side of the valve 49 back to the upstream side. Thus, the bypass section 48 serves as a safety precaution against overpressure conditions caused by the pump 14 similar to the pressure sensor assembly 76 in the embodiments of FIGS. 1 and 4. Accordingly, in the embodiment of FIG. 5, the pressure assembly 76 may be omitted. In one embodiment the bypass section 48 has a length of 5 inches, an inner diameter of ¼ inches, and an outer diameter of ⅜. The pressure relief valve has a pressure threshold of 6 psi.

Alternative Embodiments

In alternative embodiments, the sensor 16 of the irrigation apparatus 10 may be of a type that monitors a condition other than weight of the fluid reservoir 44. The sensor 16 may monitor volume of the fluid reservoir 44 via optical, mechanical, acoustic, or capacitance means.

The pump 14 may be other than a peristaltic type pump. For instance, the pump 14 may operate pneumatically, mechanically, or according to any other conventional method of transporting fluid from the plurality of fluid bags 26 to the fluid reservoir 44. Additionally, the pump 14 may be operated independently of the controller 20. For example, during the surgical procedure, a medical attendant may visually monitor the volume of fluid in the fluid reservoir 44 according to calibrations imprinted on or in the fluid reservoir 44. As the volume of the fluid reservoir 44 decreases below a pre-determined level, or when requested by the surgeon, the medical attendant may activate the pump 14. The pump 14 may be operated until the fluid reservoir 44 has been filled to the desired level.

The embodiments disclosed may incorporate one or more heating elements to heat the fluid before it is delivered to the patient. In one alternative, a heating element feature may be associated with the fluid reservoir 44. The heating element feature may take the form of a heating coil, panel, or blanket that is adjacent to or surrounding the fluid reservoir and that imparts heat to the fluid in the reservoir. In another alternative, a heating element feature may can be associated with the plurality of fluid bags 26. This heating element feature may also be provided as a coil, panel, or blanket. Either of these heating element features may be used with any of the embodiments described above. Both of these heating element features may be used in a single embodiment. When the heating element feature is used, the embodiment may also include sensors and/or thermostats. The sensors and/or thermostats are coupled to a controller, such as the controller 20, to provide for control over the temperature of the fluid being delivered to the patient. Alternatively, the heating elements may be used without sensors and operated manually.

The materials that the first tubing portion 12 and the second tubing portion 56 are composed of are not limited to one type of medical grade plastic. Also, the dimensions may 0. Additionally, the fluid in the plurality of fluid bags 26 may be saline, or any other fluid used during irrigation of a surgical procedure.

It is intended that the foregoing detailed description be regarded as illustrative rather than limiting and that it is understood that the following claims including all equivalents are intended to define the scope of the invention.

In the claims:

1. An irrigation system capable of providing a continuous supply of fluid at a relatively constant pressure from a fluid source to a surgical site, the system comprising:

a refillable fluid reservoir comprising an inlet coupled to a first tubing portion connected to the fluid source, the refillable fluid reservoir also comprising an outlet coupled to a second tubing portion leading to a surgical site;

a first sensor coupled with the refillable fluid reservoir, said first sensor is responsive to the refillable fluid reservoir and providing an output by which a need to refill the refillable fluid reservoir can be determined;

a pump coupled to the first tubing portion to cause flow of fluid from the fluid source to the refillable fluid reservoir;

an adjustable pressure applicator coupled to the refillable fluid reservoir, the adjustable pressure applicator pressurizes fluid within the refillable fluid reservoir independently of the pump so as to pressurize delivery of fluid via the second tubing portion to the surgical site; and a valve interacting with the second tubing portion for restricting fluid flow from the surgical site to the refillable fluid reservoir.

2. The irrigation system of claim 1 further comprising a controller comprising an input coupled to the output of the sensor and an output coupled to the pump, the controller adapted to control operation of the pump to cause refilling of the fluid reservoir based upon the condition of the fluid reservoir.

3. The irrigation system of claim 2 wherein the first sensor provides an output to the controller electronically.

4. The irrigation system of claim 2 further comprising a pressure sensor assembly coupled to the first tubing portion and responsive to pressure in said first tubing portion downstream of said pump, said pressure sensor assembly providing an output to the controller.

5. The irrigation system of claim 2 further comprising a second sensor associated with and monitoring the fluid source to provide an output indicative of an amount of fluid remaining in the fluid source, said second sensor providing an output to said controller.

6. The irrigation system of claim 1 wherein the first tubing portion further comprises an intermediate portion.

7. The irrigation system of claim 1 wherein the first tubing portion further comprises a proximal section, a distal section, an intermediate section located between and connecting said proximal section and the distal section, wherein said intermediate section is positioned in the pump.

8. The irrigation system of claim 7 further comprising a bypass section connecting said proximal section and the distal section in parallel with the intermediate section.

9. The irrigation system of claim 8 wherein the bypass section is located outside the pump.

10. The irrigation system of claim 8 wherein the bypass section includes a pressure valve operative to permit flow in said bypass section from the distal section to the proximal section.

11. The irrigation system of claim 10 wherein the pressure valve has a threshold of approximately 6 psi.

12. The irrigation system of claim 1 wherein the fluid source is comprised of a plurality of interconnected fluid bags.

13. The irrigation system of claim 1 wherein the pressure applicator is provided by suspending the refillable fluid reservoir from an adjustable IV pole.

14. The irrigation system of claim 1 wherein the first sensor monitors the volume of the refillable fluid reservoir.

15. The irrigation system of claim 1 wherein the first sensor monitors the weight of the refillable fluid reservoir.

16. The irrigation system of claim 1 wherein the pump is a peristaltic pump.

17. The irrigation system of claim 1 wherein the fluid source comprises saline.

18. The irrigation system of claim 1 wherein the second tubing portion is removable from the refillable fluid reservoir without compromising the sterility of the irrigation system.

19. An irrigation system for providing fluid from a fluid source to a surgical site, the system comprising:

a refillable reservoir comprising an inlet coupled to a first tubing portion connected to the fluid source, the refillable reservoir also comprising an outlet coupled to a second tubing portion leading to the surgical site;

the first tubing portion comprising a molded intermediate portion comprising a bypass device for interaction with a pump;

the second tubing portion comprising a valve for restricting fluid flow from the surgical site to the refillable reservoir;

a sensor responsive to a volume of the refillable reservoir and providing an output indicative of the volume;

a pump coupled to the first tubing portion to cause flow of fluid from the fluid source to the refillable reservoir;

a pressure applicator coupled to the refillable reservoir, the pressure applicator pressurizes fluid within the refillable fluid reservoir independently of the pump so as to pressurize delivery of fluid via the second tubing portion to the surgical site; and a controller comprising an input coupled to the output of the sensor and output coupled to the pump, the controller adapted to control operation of the pump to cause refilling of the refillable reservoir based upon the volume of the refillable reservoir.

* * * * *

UNITED STATES PATENT AND TRADEMARK OFFICE
CERTIFICATE OF CORRECTION

PATENT NO.      : 6,302,864 B1
DATED           : October 16, 2001
INVENTOR(S)     : Albert Nowosielski It is certified that error appears in the above-identified patent and that said Letters Patent is hereby corrected as shown below:

Column 8,
Line 26, delete "can be" and substitute -- is -- in its place.
Lines 50 and 51, delete "said" and substitute -- the -- in its place (all occurrences).
Lines 56 and 57, delete "said" and substitute -- the -- in its place (all occurrences).
Lines 63 and 64, delete "said" and substitute -- the -- in its place (all occurrences).
Line 66, delete "said" and substitute -- the -- in its place.

Column 9,
Line 5, delete "said" and substitute -- the -- in its place.

Signed and Sealed this

Twenty-second Day of October, 2002

*Attest:*

*Attesting Officer*

JAMES E. ROGAN
*Director of the United States Patent and Trademark Office*